United States Patent [19]
Wilk

[11] Patent Number: 5,318,515
[45] Date of Patent: Jun. 7, 1994

[54] INTRAVENOUS FLOW REGULATOR DEVICE AND ASSOCIATED METHOD

[76] Inventor: Peter J. Wilk, 185 W. End Ave., New York, N.Y. 10023

[21] Appl. No.: 931,260

[22] Filed: Aug. 17, 1992

[51] Int. Cl.$^5$ ............................................. A61M 5/175
[52] U.S. Cl. ...................................... 604/30; 604/186; 604/246; 604/250
[58] Field of Search .................. 604/186, 65–67, 604/131, 80, 81, 247, 250, 246, 30

[56] References Cited

U.S. PATENT DOCUMENTS

| | | | |
|---|---|---|---|
| 4,559,036 | 12/1985 | Wunsch | 604/250 X |
| 4,697,785 | 10/1987 | Tuseth | 604/250 X |
| 4,966,579 | 10/1990 | Polaschegg | 604/65 |
| 4,976,687 | 12/1990 | Martin | 604/246 X |
| 5,006,997 | 4/1991 | Reich | 604/65 X |

FOREIGN PATENT DOCUMENTS 9113641 9/1991 World Int. Prop. O. ............ 604/30

Primary Examiner—John D. Yasko
Attorney, Agent, or Firm—R. Neil Sudol; Henry D. Coleman

[57] ABSTRACT

A device for regulating fluid flow in an intravenous line comprises a housing and a flow path system in the housing for defining a plurality of separate flow paths having respective predetermined characteristic flow rates. The housing has an input port connectable to an intravenous line segment extending from an intravenous fluid supply and also has an output port connectable to an intravenous line segment extending to a catheter. The device additionally comprises a selector mounted to the housing and in contact with the flow path system for selectively opening the flow paths to connect the output port to the input port, thereby controlling the amount of fluid or solution flowing through the output intravenous line to a patient.

15 Claims, 2 Drawing Sheets

INTRAVENOUS FLOW REGULATOR DEVICE AND ASSOCIATED METHOD

BACKGROUND OF THE INVENTION

This invention relates to an intravenous fluid supply system. More particularly, this invention relates to a device for regulating the rate of fluid flow through an intravenous line into a patient. This invention also relates to an associated method for controlling the rate of intravenous feeding.

It is important that intravenous solutions are fed to patients at prescribed rates. A rate that is too high or too low can mean disaster to many patients, delicate conditions.

Generally, the rate of intravenous fluid flow is set by constricting a flexible tube extending from an elevated intravenous solution bag to a catheter in the patient. More specifically, the constriction is accomplished by pushing a valve member to pinch the flexible intravenous tube between the valve member and a tapered ramp extending through a housing. To set a desired rate, one views a drip chamber upstream of the valve member. The valve is adjusted until a prescribed number of drips per time unit is counted at the drip chamber.

This conventional rate setting method is inaccurate and prone to error. Nurses frequently do not have the opportunity to accurately monitor the flow rate prior to a final selection.

OBJECTS OF THE INVENTION

An object of the present invention is to provide an improved method for setting an intravenous flow rate.

Another object of the present invention is to provide such a method which results in increased accuracy.

Another, more particular, object of the present invention is to provide such a method which is easy and quick to implement.

An associated object of the present invention is to provide a device connectable in an intravenous flow line for facilitating the setting of flow rate.

Yet another particular object of the present invention is to provide an intravenous flow rate regulator which is inexpensive to manufacture.

These and other objects of the invention will be apparent from the descriptions and illustrations provided herein.

SUMMARY OF THE INVENTION

A device for regulating fluid flow in an intravenous line comprises, in accordance with one conceptualization of the present invention, a housing and a flow path system in the housing for defining a plurality of separate flow paths having respective predetermined characteristic flow rates. The housing has an input port connectable to an intravenous line segment extending from an intravenous fluid supply and also has an output port connectable to an intravenous line segment extending to a catheter. The device additionally comprises a selector mounted to the housing and in contact with the flow path system for selectively opening the flow paths to connect the output port to the input port, thereby controlling the amount of fluid or solution flowing through the output intravenous line to a patient.

Pursuant to one embodiment of the present invention, the flow path system includes a plurality of resilient tubes connected in parallel to one another in a manifold, the tubes having respective cross-sectional areas. In that event, the selector may include a blocking mechanism for collapsing the tubes to close the tubes. More specifically, The blocking mechanism includes parts of a plurality of toggle switches in contact with respective tubes of the flow path system. Preferably, the cross-sectional areas of the tubes of the flow path system are different from each other.

Pursuant to another embodiment of the present invention, the flow path system includes a plurality of divided tubes each associated with a respective one of the flow paths, the characteristic flow rates of each divided tube being different from the characteristic flow rates of the other tubes in the flow path system. The selector then includes means for selectively permitting fluid flow through only one of the divided tubes. More specifically, upon selection and implementation of a desired flow rate in an intravenous line, all of the tubes except one are blocked, the opened tube being aligned with a bridging duct with connects downstream and upstream parts of the tube. The bridging duct may be provided in a sliding member which automatically blocks all tubes other than the tube having the selected flow rate.

Pursuant to a further embodiment of the present invention, the selector includes a plurality of spring loaded valves associated with respective flow paths, the selector further including an actuator movably mounted to the housing for selectively opening the valves.

In yet another embodiment of the present invention, the selector includes a plurality of frangible seals associated with respective flow paths, the selector further including an actuator movably mounted to the housing for selectively breaking the seals.

Pursuant to one feature of the present invention, the characteristic flow rates of the different flow paths of the flow path system are different from each other. Alternatively, the characteristic flow rates are uniform, the selector including means for selectively opening a plurality of the flow paths simultaneously. Where the characteristic flow rates are different, multiple flow paths of the flow path system may be connected between the input port and the output port, thereby providing a greater selection of possible flow rates.

Pursuant to another feature of the present invention, indicators are provided on the housing for indicating different flow rates at different operative positions of the selector.

A method for use in intravenous feeding comprises, in accordance with the present invention, the steps of (a) inserting an intravenous catheter into a patient, (b) connecting an intravenous supply to an inlet side of a flow regulator, (c) opening at least one of plurality of possible flow paths through the flow regulator to connect the inlet side of the flow regulator to the outlet side thereof, and (d) connecting the catheter to an outlet side of the flow regulator. The flow paths have predetermined characteristic flow rates which may be the same or different from each other.

According to another feature of the present invention, the step of opening one or more flow paths includes the step of pivoting a toggle switch to unclamp a flexible tube.

According to an alternative feature of the present invention, the step of opening one or more fluid flow paths includes the step of shifting a slider member in the flow regulator to connect an input tube to an output tube.

According to another alternative feature of the present invention, the step of opening one or more fluid flow paths includes the step of opening one of a plurality of distinct valve elements.

According to yet another alternative feature of the present invention, the step of opening one or more fluid flow paths includes the step of breaking one of a plurality of distinct seal elements.

A device for regulating fluid flow in an intravenous line comprises, in accordance with another conceptualization of the present invention, a housing, a flow path system in the housing for defining a plurality of separate flow paths having respective predetermined characteristic flow rates, an input port on the housing connectable to an intravenous line extending from an intravenous fluid supply, and an output port on the housing connectable to an intravenous line extending to a catheter. The input port communicates with the flow path system on an inlet side thereof, while the output port communicates with the flow path system on an outlet side thereof. A closure element or elements are mounted to the housing and in contact with the flow path system for closing the flow paths and thereby blocking fluid flow therethrough, and a selector or selectors are mounted to the housing for selectively releasing the closure elements to selectively open the flow paths to connect the output port to the input port.

Pursuant to another feature of the present invention, the flow path system includes a plurality of resilient tubes connected in parallel to one another in a manifold, the tubes having respective cross-sectional areas. The closure elements serve to block or collapse the tubes and may include lever elements of a plurality of toggle switches, the lever elements being in contact with respective resilient tubes.

The present invention provides an improved method for setting an intravenous flow rate. The method provides for increased accuracy and is easy and quick to implement.

DETAILED DESCRIPTION

Figure 1:
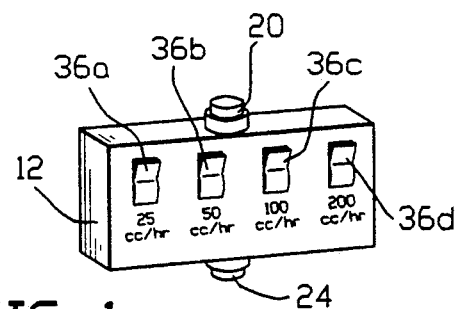
FIG. 1 is a schematic isometric view of an intravenous flow regulator device in accordance with the present invention.
Figure 2:
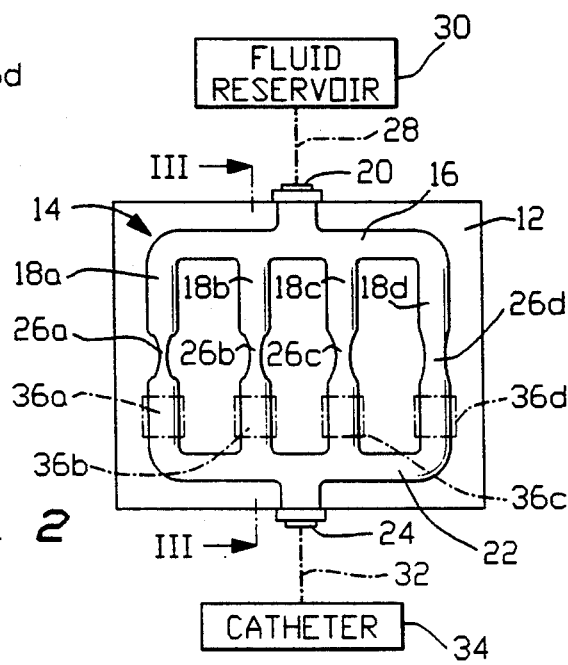
FIG. 2 is a diagram illustrating components of the flow regulator device of FIG. 1.

As illustrated in FIGS. 1 and 2, a device for regulating fluid flow in an intravenous line comprises a housing 12 and a flow path system 14 in the housing. Flow path system 14 includes an input manifold 16 which connects a plurality of resilient or flexible tubes 18a, 18b, 18c, 18d to an input port 20 and an output manifold 22 which connects tubes 18a, 18b, 18c, 18d to an output port 24. Tubes 18a, 18b, 18c, 18d define respective separate flow paths having respective predetermined characteristic flow rates. More particularly, tubes 18a, 18b, 18c, 18d incorporate narrowed sections 26a, 26b, 26c, 26d of differing cross-sectional areas which present different flow resistances and therefore give rise to respective different flow rates. Fluid flows through individual tubes 18a, 18b, 18c, 18d at respective rates, for example, of 25 cc/hr, 50 cc/hr, 100 cc/hr, and 200 cc/hr.

Input port 20 is connectable to an intravenous line segment 28 extending from an intravenous fluid supply 30, while output port 24 is connectable to an intravenous line segment 32 extending to a catheter 34. A plurality of selectors in the form of toggle switches or buttons 36a, 36b, 36c, 36d are mounted to housing 12 and are in contact with respective tubes 18a, 18b, 18c, 18d of flow path system 14 for selectively opening the flow paths thereof to connect output port 24 to input port 20. Toggle switches 36a, 36b, 36c, and 36d enable a user to control amount of fluid or solution flowing through intravenous line segment 32 to a patient.

Figure 3:
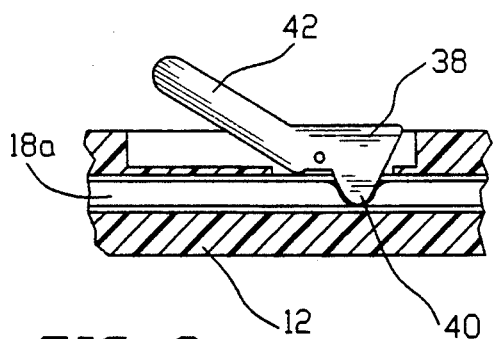
FIG. 3 is a partial cross-sectional view taken along line III—III in FIG. 2.

As illustrated in FIG. 3, toggle switches 36a, 36b, 36c, 36d each include a first lever 38 provided with a projection 40 which is engageable with a respective tube 18a, 18b, 18c, 18d in an "off" or closed position of the switch to clamp or block the respective tube. Prior to use, every toggle switch 36a, 36b, 36c, 36d is set in a closed configuration, as shown in FIG. 1. Each toggle switch 36a, 36b, 36c, 36d further includes a second lever 42 which is pressed in order to open the respective tube or fluid flow path 18a, 18b, 18c, 18d.

In using the intravenous flow regulator of FIGS. 1 and 2, catheter 34 is inserted into a vein or artery of a patient. Intravenous fluid reservoir or bag 30 is connected to input port 20 via intravenous line segment 28, while intravenous line segment 32 is connected to output port 24. Catheter 34 is coupled to output port 24 via line segment 32. At least one tube or flow path 18a, 18b, 18c, or 18d through the flow regulator is then opened by pushing the "on" lever 42 of the respective toggle switch 36a, 36b, 36c, 36d. Of course, the desired flow path opened and the output line segment 32 is flushed preferably prior to connection thereof to catheter 34, to clear the line of air bubbles.

It is to be noted that flow path system 14 is designed so that a plurality of toggle switches 36a, 36b, 36c, 36d may be actuated to open a plurality of tubes or fluid flow paths 18a, 18b, 18c, 18d, thereby providing a greater range of possible flow rates. For example, toggle switches 36a, 36b, and 36c may be pressed to open tubes 18a, 18b, and 18c, thereby setting a flow rate of 175 cc/hr, equal to the combined flow rates of the three tubes.

Figure 4:
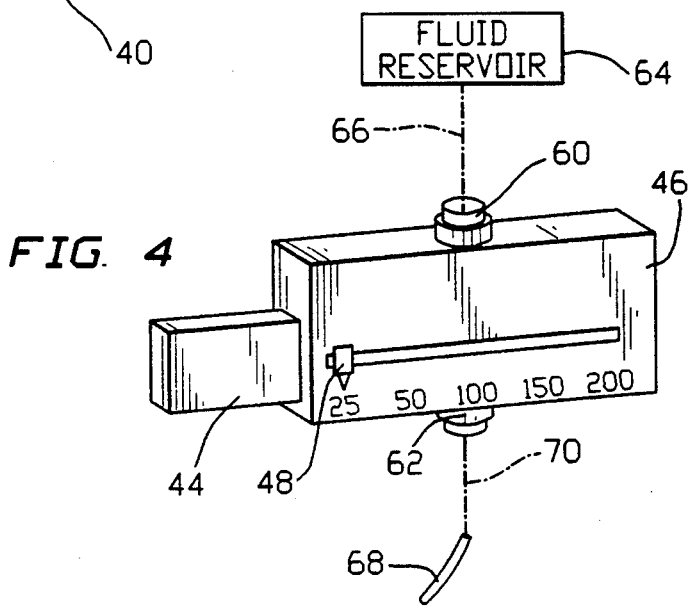
FIG. 4 is a schematic isometric view of another intravenous flow regulator device in accordance with the present invention.
Figure 5:
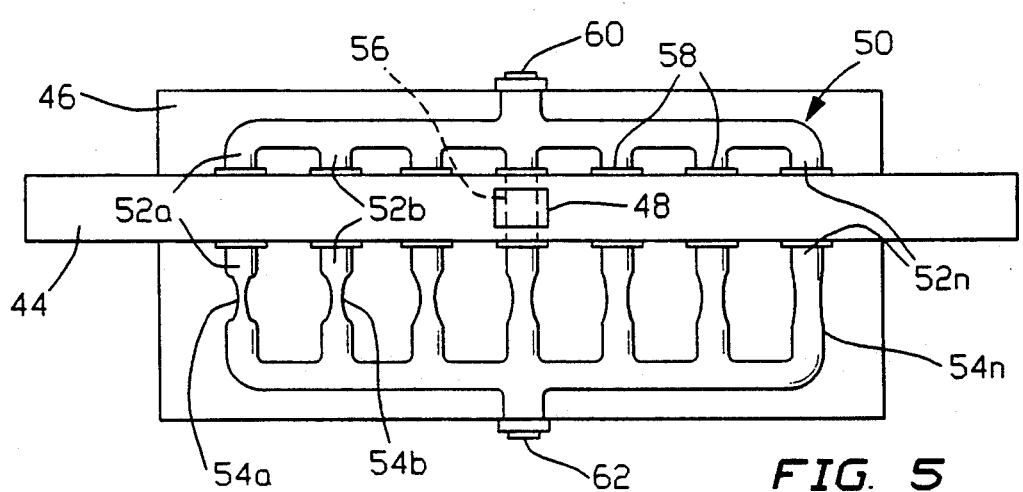
FIG. 5 is a diagram illustrating components of the flow regulator device of FIG. 4.

As illustrated in FIGS. 4 and 5, in another intravenous flow regulator, a slider member 44 is slidably disposed in a housing 46 for setting or selecting a desired flow rate. Slider member is provided with a pusher 48 which is used to shift the slider to select a desired flow rate and which additionally serves as a pointer indicating a selected fluid flow rate. Housing 46 carries a flow path system 50 including a plurality of divided tubes 52a, 52b, . . . 52n each defining a respective flow path having a respective characteristic flow rate different from the characteristic flow rates of the other tubes in flow path system 50. The different flow rates may be achieved, for example, by providing tubes 52a, 52b . . .

52n with segments 54a, 54b, . . . 54n of reduced cross-section and different resistances to fluid flow.

Slider member 44 serves for selectively permitting fluid flow through only one of divided tubes 52a, 52b . . . 52n. To that end, slider member 44 is provided with a single duct or channel 56 which is alignable with any one of tubes 52a, 52b . . . 52n, depending on the position of slider member 44. Slider member 44 serves to block fluid flow through the other tubes 52a, 52b . . . 52n. Tubes 52a, 52b . . . 52n are provided with sealing rings 58 which engage slider member 44 to effectuate a fluid tight seal therewith.

As illustrated in FIG. 5, tubes 52a, 52b . . . 52n are connected on an inlet side to an input port 60 on housing 46 and on an outlet side to an output port 62 on the housing. As illustrated in FIG. 4, input port 60 is connectable to an intravenous fluid reservoir or supply 64 via an inlet line segment 66 and to an intravenous catheter 68 via an outlet line segment 70.

Upon selection and implementation of a desired flow rate in the intravenous line extending from supply 64 to catheter 68, all tubes 52a, 52b . . . 52n except one are blocked by slider member 44. The opened tube is aligned with bridging duct 56 with connects downstream and upstream parts of that tube, as indicated in FIG. 5

It is to be noted that housing 46 may enclose slider member 44 in its entirety, which particularly enhances sterility.

The intravenous flow regulator of FIGS. 4 and 5 is used in a manner similar to the use of the flow regulator of FIGS. 1 and 2. In the embodiment of FIGS. 4 and 5, only one tube 52a, 52b . . . 52n can be opened at any one time. Therefore, many tubes 52a, 52b . . . 52n must be provided if it is desired to increase the range of selectable flow rates.

Figure 6:
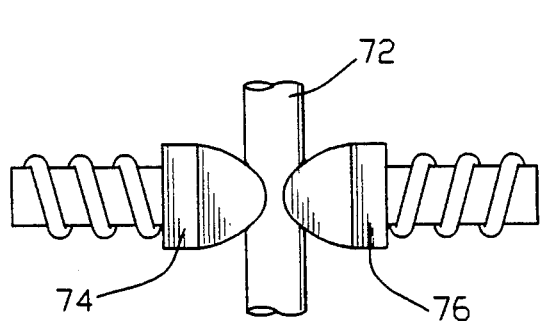
FIG. 6 is a schematic partial top view of flow control components of yet another flow regulator device in accordance with the present invention.
Figure 7:
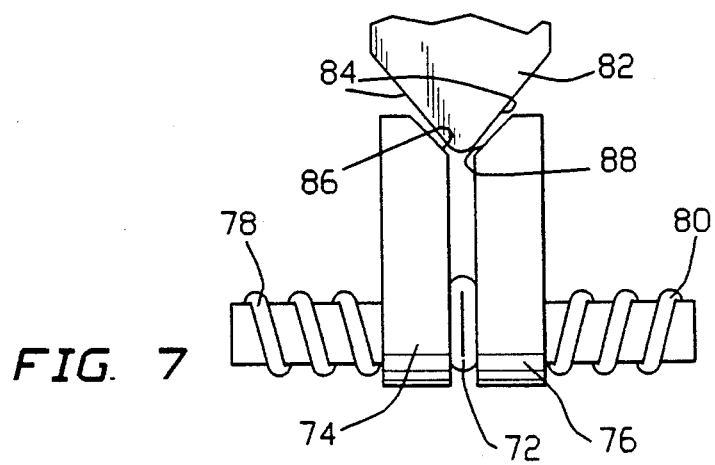
FIG. 7 is a side elevational view of the flow control components of FIG. 6.

As depicted in FIGS. 6 and 7, another intravenous flow rate regulator may be provided with a plurality of tubes 72 (only one shown) connected in parallel to one another by a manifold (not shown). Each tube 72 is closed or blocked by one or two clamping members 74 and 76 slidably mounted to a housing (not illustrated) and biased into contact with tube 72 by respective springs 78 and 80. Each tube 72 represents a characteristic flow rate different from the flow rates of the other tubes. Clamping members 74 and 76 are spring loaded valves associated with respective flow paths.

In the flow regulator embodiment of FIGS. 6 and 7, a selector in the form of a spring loaded button 82 is slidably mounted to the housing. Upon a sliding of the button to the desired tube 72, button 82 is pressed so that camming surfaces 84 thereon cam against camming surfaces 86 and 88 of clamping members 74 and 76, thereby separating the clamping members in opposition to the closure forces exerted by springs 78 and 80 and opening the respective fluid flow tube 72. Button 82 may be provided with a detent or latch (not illustrated) for securing the button to the housing upon an actuation of the button.

Figure 8:
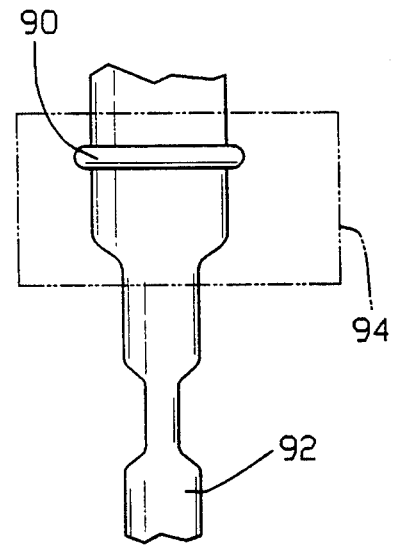
FIG. 8 is a schematic partial top view of flow control components of yet a further flow regulator device in accordance with the present invention.

In an embodiment of a flow regulator depicted in part in FIG. 8, a selector mechanism includes a plurality of frangible seals 90 (only one shown) associated with respective tubular flow paths 92 (only one shown). The selector mechanism further including an actuator 94 movably mounted to a housing (not shown) for selectively breaking the seals.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A device for regulating fluid flow in an intravenous line, comprising:
   a housing;
   flow path means in said housing for defining a plurality of separate flow paths having respective predetermined characteristic flow rates different from each other, said flow path means including a plurality of resilient tubes connected in parallel to one another in a manifold, said tubes having respective cross-sectional areas different in size from each other;
   an input port on said housing connectable to an intravenous line extending form an intravenous fluid supply;
   an output port on said housing connectable to an intravenous line extending to a catheter; and
   selector means mounted to said housing and in contact with said flow path means for selectively opening said flow paths to connect said output port to said input port.

2. The device defined in claim 1 wherein said selector means includes blocking mean for collapsing said tubes to close same.

3. The device defined in claim 2 wherein said blocking means includes a plurality of toggle switches each in contact with a respective one of said tubes.

4. The device defined in claim 1 wherein said selector means includes means for selectively permitting fluid flow through only one of said tubes.

5. The device defined in claim 1 wherein said selector means includes a plurality of spring loaded valves associated with respective ones of said flow paths, said selector means further comprising actuator means movably mounted to said housing for selectively opening said valves.

6. The device defined in claim 1 wherein said selector means includes means for selectively opening a plurality of said flow paths simultaneously.

7. The device defined in claim 1, further comprising indicator means on said housing for indicating different flow rates at different operative positions of said selector means.

8. A method for use in intravenous feeding, comprising the steps of:
   inserting an intravenous catheter into a patient;
   connecting an intravenous supply to an inlet side of a flow regulator including a plurality of flexible tubes each deformably collapsed at a point along the respective tube;
   deformably opening at least one of said flexible tubes to open at least one of plurality of corresponding flow paths through said flow regulator to connect the inlet side of the flow regulator to the outlet side thereof, said flow paths having respective predetermined characteristic flow rates different from each other; and
   connecting said catheter to an outlet side of said flow regulator.

9. The device defined in claim 8 wherein said step of opening includes the step of pivoting a toggle switch to unclamp a flexible tube.

10. The device defined in claim 8 wherein said step of opening includes the step of opening one of a plurality of distinct valve elements.

11. A device for regulating fluid flow in an intravenous line, comprising:

a housing;

flow path means in said housing for defining a plurality of separate flow paths having respective predetermined characteristic flow rates different from each other, said flow path means including a plurality of resilient tubes connected in parallel to one another in a manifold, said tubes having respective cross-sectional areas different in size from each other;

an input port on said housing connectable to an intravenous line extending form an intravenous fluid supply, said input port communicating with said flow path means on an inlet side thereof;

an output port on said housing connectable to an intravenous line extending to a catheter, said output port communicating with said flow path means on an outlet side thereof;

closure means mounted to said housing and in contact with said flow path means for closing said flow paths and thereby blocking fluid flow therethrough; and selector means mounted to said housing for selectively releasing said closure means to selectively open said flow paths to connect said output port to said input port.

12. The device defined in claim 11 wherein said closure means includes blocking means for collapsing said tubes to close same.

13. The device defined in claim 12 wherein said blocking means includes lever elements of a plurality of toggle switches, said lever elements being in contact with respective ones of said tubes.

14. The device defined in claim 11 wherein said characteristic flow rates are uniform, said selector means including means for selectively opening a plurality of said flow paths simultaneously.

15. The device defined in claim 11, further comprising indicator means on said housing for indicating different flow rates at different operative positions of said selector means.

* * * * *

UNITED STATES PATENT AND TRADEMARK OFFICE
CERTIFICATE OF CORRECTION

PATENT NO. : 5,318,515
DATED : June 7, 1994
INVENTOR(S) : Peter J. Wilk

It is certified that error appears in the above-indentified patent and that said Letters Patent is hereby corrected as shown below:

Column 1, line 14, change "," (comma) after "patients" to --'-- (apostrophe).
Column 2, line 53, insert --a-- after "of" (first occurrence).
Column 4, line 44, insert --is-- after "path"; line 59, insert --44-- after "member".
Column 6, line 22, change "form" to --from--; line 31, change "mean" to --means--; line 61, insert --a-- after "of" (1st occurrence)
Column 7, line 21, change "form" to --from--; line 31,
Column 8, line 18, delete "said char-"; line 19, delete "acteristic flow rates are uniform,"; line 20, change "including" to --includes--

Signed and Sealed this

Fourteenth Day of March, 1995

Attest:

BRUCE LEHMAN

Attesting Officer

Commissioner of Patents and Trademarks